United States Patent [19]

Lange

[11] Patent Number: 4,801,798

[45] Date of Patent: Jan. 31, 1989

[54] METHOD AND APPARATUS FOR MEASURING OPTICAL RETARDATION IN TRANSPARENT MATERIALS

[75] Inventor: Gerald R. Lange, Rochester, N.Y.

[73] Assignee: Eastman Kodak Company, Rochester, N.Y.

[21] Appl. No.: 133,112

[22] Filed: Dec. 14, 1987

[51] Int. Cl.$^4$ ............................................. G01N 21/21
[52] U.S. Cl. .................................... 250/225; 356/367
[58] Field of Search ................. 250/225; 356/364, 365, 356/366, 367, 369, 370, 33–35

[56] References Cited

PUBLICATIONS

Azzam, *Optics Communications*, vol. 20, No. 3, Mar. 1977, pp. 405–408.
Zaghloul, *Optics Communications*, vol. 27, No. 1, Oct. 1978, pp. 1–3.

*Primary Examiner*—F. L. Evans
*Attorney, Agent, or Firm*—Warren W. Kurz

[57] ABSTRACT

A method and apparatus for measuring optical retardation of a transparent material, such as the protective transparent cover sheet or substrate which protects the recording layer of an optical or magneto-optical disk. The method of the invention involves the steps of producing a beam of plane-polarized radiation in which the plane of polarization rotates continuously, directing such beam through a sample of transparent material where optical retardation is to be measured, and continuously comparing the angle of polarization of the beam entering the sample with the angle of plane polarization of the beam exiting the sample. Preferably, the beam and sample are continuously moved relative to another, whereby the optical retardation is measured at different points on the sample. The beam-producing step may be effected by passing a beam of circularly polarized radiation through a plane-polarizing filter while continuously rotating the filter. In this case, the comparing step may be achieved by (a) redirecting the beam exiting the sample back through the rotating filter and (b) monitoring the intensity of the beam after passing back through such filter.

9 Claims, 1 Drawing Sheet

METHOD AND APPARATUS FOR MEASURING OPTICAL RETARDATION IN TRANSPARENT MATERIALS

BACKGROUND OF THE INVENTION

This invention relates to method and apparatus for detecting and measuring optical retardation in transparent materials. The method and apparatus of the invention are particularly well suited for measuring optical retardation variations in a transparent sheet whose thickness and/or birefringence may vary from point-to-point over the area of the sheet.

For a variety of reasons, it is often desirable to measure the optical retardation in a sheet of transparent material. For example, in the field of optical recording, the recording layer of an optical disk is usually protected from dust and dirt by a transparent cover sheet or substrate. To recover the information recorded on the optical disk, a plane-polarized beam, as produced by a laser, is directed at the recording layer through the protective, transparent cover sheet or substrate. Upon being reflected by the recording layer (or a reflective layer underlying the recording layer) the laser beam is directed to a photodetector which senses the data-produced intensity variations of the beam. To isolate the laser cavity from radiation reflected from the disk during readout, it is common to employ the combination of a polarizing beam-splitter and a quarter-wave plate. Radiation from the read laser is polarized in a given plane which allows it to pass through the polarizing beam-splitter. Such plane-polarized beam is then circularly polarized in a, say, clockwise sense by passing it through the quarter-wave plate. Upon being reflected from the disk, the beam becomes circularly polarized in the opposite sense and, upon passing through the quarter-wave plate a second time, becomes plane polarized at an angle perpendicular to the plane of polarization passed by the polarizing beam-splitter. Upon striking the beam-splitter the second time with its plane of polarization perpendicular to that passed by the beam splitter, 100% of the beam is reflected to the photodetector. Obviously, if the state of polarization of the radiation returning to the beam-splitter is anything other than plane-polarized in a direction perpendicular to that passed by the beam-splitter, the beam-splitter will pass a portion of such radiation back to the laser cavity, causing undesired variations in the laser output and, moreover, effecting a reduction and modulation of the radiation striking the data and servo detectors. Any optical retardation of the beam between the two passes through the quarter-wave plate will cause some degree of ellipticity in the polarization of the beam, and some energy will return to the laser cavity. A major source of such retardation is birefringence in the protective transparent layer of the optical disk. Such birefringence can be produced during the manufacture of the transparent layer or can be produced by non-uniform stressing of the layer during assembly of the disk. Before an optical disk is approved for shipping, core must be taken that the optical retardation introduced by the transparent protective layers meets certain strict standards. Preferably, the optical retardation introduced by the transparent layers should be no greater than 0.1 λ (i.e., the wavelength of the readout laser (830 nm.)).

A known method for measuring the amount of retardation in an optical element is a point-by-point technique which makes use of a device known as a polariscope. According to this method, the beam is passed through both the sample and the polariscope, and the polariscope is adjusted to add an equal and opposite amount of retardation so that the net effect is zero retardation. To do this, it is necessary to precisely align the optical axes of the sample and the polariscope 90° apart. This presents no problem when measuring the retardation of a single point on the sample; however, when it is desired to make measurements at, say, a 1000 points over the surface of the sample, this technique is extremely time-consuming and operator-dependent for accuracy.

SUMMARY OF THE INVENTION

In view of the foregoing, an object of this invention is to provide a method and apparatus for making a rapid and highly reliable measurements of the optical retardation at a multiplicity of points on a transparent element.

The method of the invention involves the steps of producing a beam of plane-polarized radiation in which the plane of polarization rotates continuously, directing such beam through the transparent element, and comparing the angle of plane polarization of the beam entering the element with the angle of plane polarization of the beam exiting such element. The apparatus of the invention comprises means for producing a beam of plane polarized radiation in which the plane of polarization rotates continuously, means for directing such beam through a transparent layer whose optical retardation is to be measured, and means for comparing the angle of plane polarization of the beam entering the layer with the angle of plane polarization of the beam exiting the layer.

The invention will be better understood from the ensuing detailed description of preferred embodiments, reference being made to the accompanying drawings.

DETAILED DESCRIPTION OF PREFERRED EMBODIMENTS

Figure 1:
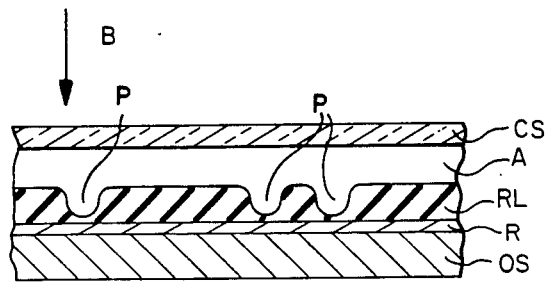
FIGS. 1 and 2 are cross-sectional illustrations of conventional optical disk assemblies.
Figure 2:
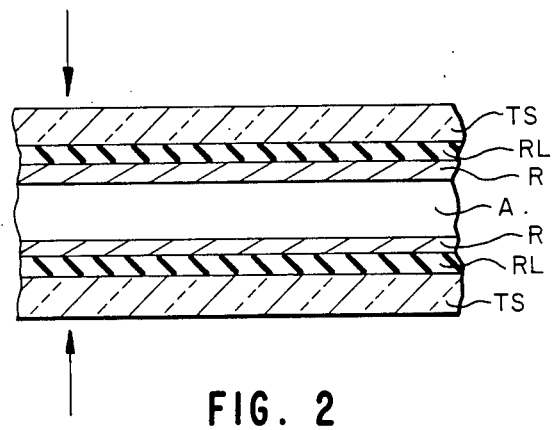

Referring to the drawings, FIGS. 1 and 2 are fragmentary cross-sectional illustrations of conventional optical disks. In the FIG. 1 illustration, the optical disk is shown to comprise a rigid opaque substrate OS having a reflective layer R thereon. A recording layer RL overlies the reflective layer and comprises, for example, a die/binder material. When subjected to an intensity-modulated laser beam of suitable intensity, pits P representing recording information, are ablated in recording layer. These pits are optically detected by scanning the recording layer with a non-modulated beam B of radiation and detecting the radiation reflected from the reflective surface which underlies the recording layer. To protect the recording layer from dust and dirt as well as to displace such dust and dirt particles out of the focal plane of the read/write laser beam, a transparent cover sheet CS may be provided. Such cover sheet may be physically separated from the recording layer by an airspace A. Alternatively, the protective cover sheet may comprise a relatively thick transparent layer formed directly on the recording layer.

In FIG. 2, another form of optical disk is shown to comprise a pair of confronting transparent substrates TS separated by airspace A. Each substrate TS is provided, as above, with a recording layer RL which, in this case, is overcoated with a reflective layer R. Here again, recording and playback are effected through a transparent element, in this case, the transparent substrate TS.

In optical disk structures of the type described above, it is essential that the transparent elements CS and TS exhibit relatively low optical retardation, preferably, less than one-tenth of the wavelength of the laser beam used to readout the recorded information; otherwise, as noted above, the plane polarization of the read beam will be altered to the extent that a portion of the beam will return to the laser cavity undesired intensity variations of the laser beam, as well as undesired variations in the level of radiation reaching the data and servo detectors.

According to present invention, there is provided a method and apparatus for rapidly and reliably measuring the optical retardation of transparent elements, such as the transparent cover sheet and substrates in the above optical disk assemblies. The method lends itself to producing continuous curves of double pass retardation measurements at a multitude of points along a path, for example, the circular path defined by a constant radius about a point. Importantly, the method of the invention is inherently insensitive to the orientation of the major and minor axes of the sample whose retardation is being measured. In addition, it is self-calibrating.

Figure 3:
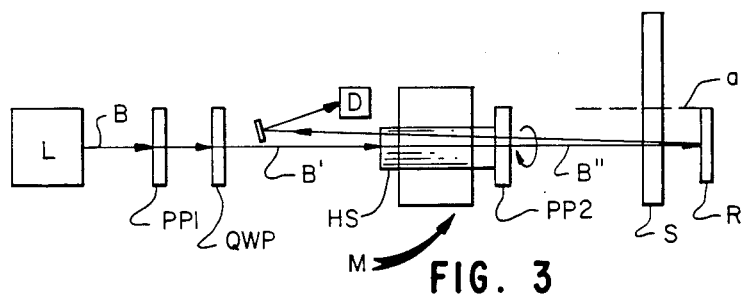
FIG. 3 is a schematic illustration of preferred apparatus for implementing the method of the invention.

Referring to FIG. 3 which schematically illustrates preferred apparatus for implementing the method of invention, a beam B of monochromatic radiation emanating from a laser L, such as a helium-neon laser, is first passed through a plane-polarizing element PP1. Element PP1 simply assures the plane-polarization of beam B. The beam exiting element PP1 is then passed through a quarter-wave plate QWP to produce a beam B' of circularly polarized radiation in which the intensity of the beam is equal at all angles of polarization. Beam B' then passes through a second plane-polarizing element PP2 which is rotating at a moderate rate (e.g. 1000 rpm) about an axis normal to its surface. Plane-polarizing element PP2 is rigidly coupled to one end of a hollow shaft HS which is rotatably driven by a motor M. Beam B' is directed through the hollow shaft to element PP1. As the plane-polarizing element PP2 rotates at a constant rate, the angle of polarization of the beam B" exiting element PP2 rotates at a corresponding rate. Beam B" is then directed through the transparent sample whose retardation is to be measured, whereupon it strikes a reflector R positioned at a slight angle relative to the path of travel of the incident beam. Upon reflecting from the reflective surface R, beam B" passes again through the sample S and back through the plane polarizing element PP2 to a photodetector D.

In using the above apparatus, it will be appreciated that, in the event that portion of the sample through which beam B" passes produces no optical retardation, the plane of polarization of beam B" will be the same both before and after it interacts with the sample. Since the polarizer PP2 is rotating slowly, relative to the travel time of radiation to and from the reflector R, the beam will pass back through the polarizer unaffected. Of course, some attenuation occurs due to the density characteristics of polarizers, but this change in intensity is a constant. If, on the other hand, the sample causes a certain amount of optical retardation, for example, one-half wavelength after passing through the sample twice, then the output of detector D will be modulated in intensity, such modulation being at a frequency four times that of the rotation rate of element PP2. When the plane of polarization of beam B" as it strikes the sample is parallel with either of the optical axis (major or minor) of the sample, no retardation will occur and the return beam will be unimpeded by polarizer PP2, as in the case where the sample introduces no retardation. However, when the plane of polarization of beam B" as it strikes the sample is at 45° to the sample's axes, the plane of polarization of the beam emerging from the sample will be rotated 90° relative to the incident beam due to the sample's retardation. In this case, the beam is completely blocked by the rotating polarizer PP2. As will be appreciated, during each rotation of the polarizer PP2, there will be a 100% modulation of the beam intensity, such modulation occurring, as noted above, at four times the revolution rate of the polarizer. If the sample has a ¼ wave retardation, the beam sensed by detector D will be modulated by 50%. Obviously, the amount of modulation of the beam intensity sensed by the photo detector is proportional to the retardation introduced by the sample. The relationship between modulation, M, and retardation, R, is given by the relationship:

$$\text{Modulation} = [\cos(\pi R/\lambda)]^2$$

The output of detector D may be sampled rapidly (e.g. 1000 samples/sec.) by a computer-controlled voltmeter. The amount of modulation is then calculated by the computer and converted to retardation. If, during the measurement, the sample is moved, such as rotated about axes a, to allow the beam to scan the sample, then a continuous trace of retardation along the scan path is produced.

When using the above scheme to measure the optical retardation present in the transparent cover sheet or substrate of an optical disk assembly, the optical disk assembly is positioned in the path of beam B". The disk is then rotated, for example, at 0.75 rpm, so that the optical retardation can be measured at any desired radius on the disk. In this manner, a continuous trace of the optical retardation at a given radius is provided and, based on the depth of modulation of the signal, it may be determined whether the transparent cover sheet or substrate meets certain minimum standards.

The method for measuring optical retardation described above has proven to be highly advantageous over the traditional point-by-point methods. In use, it has been found to be highly reliable, accurate, fast, operator-independent, and easily automated.

The invention has been described in detail with particular reference to preferred embodiments thereof, but it will be understood that variations and modifications can be effected within the spirit and scope of the invention.

I claim:

1. A method for measuring optical retardation of a transparent element, said method comprising the steps of:
   (a) producing a beam of plane-polarized radiation in which the plane of polarization rotates continuously;
   (b) directing such beam through a transparent element; and (c) continuously comparing the angle of plane polarization of the beam entering the element with the angle of plane polarization of the beam exiting the element.

2. The method as defined by claim 1 wherein said beam-producing step comprises the step of passing a beam of circularly polarized radiation through a plane-polarizing filter while rotating the plane of polarization of such filter.

3. The method as defined by claim 2 wherein said comparing step comprises the steps of (a) redirecting the beam exiting the element back through said filter and (b) monitoring the intensity of the beam after passing back through said filter.

4. The method as defined by claim 3 wherein said re-directing step comprises the step of reflecting the beam exiting the element back through such element.

5. Apparatus for measuring optical retardation of transparent materials, said apparatus comprising:
   (a) means for producing a plane-polarized beam of radiation in which the plane of polarization continuously rotates.
   (b) means for directing such beam through a transparent sample whose optical retardation is to be measured; and
   (c) means for continuously comparing the angle of plane polarization of the beam entering the sample with the angle of plane-polarization of the beam exiting the sample.

6. The apparatus as defined by claim 5 wherein said producing means comprises (a) means for producing a beam of circularly polarized radiation, (b) polarizing filter means positioned in said beam of circularly polarized radiation for converting said beam of circularly polarized radiation to a beam of plane-polarized radiation and (c) means for rotating said polarizing filter means.

7. The apparatus as defined by claim 6 wherein said comparing means comprises means for directing the beam exiting the sample back through said polarizing filter means, and means for monitoring the intensity of the beam after passing back through said filter means.

8. Apparatus for measuring optical retardation in a birefringent membrane overlying a reflective surface, said apparatus comprising:
   (a) means for producing a beam of circularly polarized radiation;
   (b) polarizing filter means located in said beam for converting said circularly polarized radiation to a first beam of plane-polarized radiation;
   (c) means for rotating said polarizing filter means to cause the plane of polarization of said first beam to rotate continuously;
   (d) means for scanning a birefringent membrane overlying a reflective surface with said first beam to cause said first beam to pass through said membrane, reflect from said surface and pass again through said membrane, whereby a second beam of plane-polarized radiation is produced, the plane of polarization of said second beam being angularly displaced with respect to the plane of polarization of said first beam proportional to the amount of optical retardation; and
   (e) means for continuously monitoring the angle between the respective planes of polarization of said first and second beams.

9. The apparatus as defined by claim 8 wherein said monitoring means comprises means for passing said second beam back through said polarizing filter means, and means for detecting the intensity of said second beam after being passed by said polarizing filter means.

* * * * *